United States Patent [19]

Böshagen et al.

[11] Patent Number: 4,806,667

[45] Date of Patent: * Feb. 21, 1989

[54] PROMOTING PRODUCTION OF USEFUL LIVESTOCK WITH SILYLATED AMINOPHENYLETHYLAMINE DERIVATIVES

[75] Inventors: Horst Böshagen; Jürgen Stoltefuss, both fo Haan; Friedrich Berschauer, Wuppertal; Anno de Jong, Wuppertal; Martin Scheer, Wuppertal, all of Fed. Rep. of Germany

[73] Assignee: Bayer Aktiengesellschaft, Leverkusen, Fed. Rep. of Germany

[*] Notice: The portion of the term of this patent subsequent to Jun. 2, 2004 has been disclaimed.

[21] Appl. No.: 937,759

[22] Filed: Dec. 4, 1986

Related U.S. Application Data

[63] Continuation-in-part of Ser. No. 709,624, Mar. 8, 1985, Pat. No. 4,670,423.

[30] Foreign Application Priority Data

Dec. 11, 1985 [DE] Fed. Rep. of Germany ....... 3543636
Dec. 11, 1985 [DE] Fed. Rep. of Germany ....... 3543637
Mar. 22, 1986 [DE] Fed. Rep. of Germany ....... 3609812

[51] Int. Cl.$^4$ .............................................. C07F 7/10
[52] U.S. Cl. ................... 556/424; 556/413; 556/417; 564/363; 564/364
[58] Field of Search ....................... 556/413, 417, 424; 514/63, 653, 524; 564/363, 364

[56] References Cited

U.S. PATENT DOCUMENTS 3,574,211  4/1971  Kock et al. ........................ 564/363
4,063,025  12/1977  Murakami et al. .............. 564/363 X
4,670,423  6/1987  Böshagen et al. ................. 556/413

FOREIGN PATENT DOCUMENTS 0154923  9/1985  European Pat. Off. ............ 556/413

*Primary Examiner*—Paul F. Shaver
*Attorney, Agent, or Firm*—Sprung Horn Kramer & Woods

[57] ABSTRACT

A method for promoting production of useful livestock comprising administering to such livestock an amount effective therefor of a monosilylated aminopheylethylamine derivative of the formula

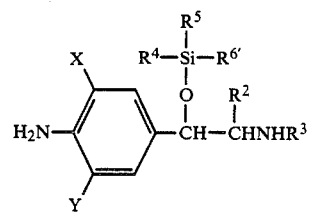

in which X and Y are identical or different and represent hydrogen or CN, $R^2$ represents hydrogen or methyl, $R^3$ represents t-butyl, isopropyl, monofluoro-t-butyl or 1-cyclohexyl-ethyl, and $R^4$, $R^5$ and $R^6$ denote a straight-chain or branched alkyl rdical, or a physiologically tolerated salt thereof.

Those compounds wherein $R^3$ is monofluoro-t-butyl or 1-cyclohexyl-ethyl are new, as is its intermediate

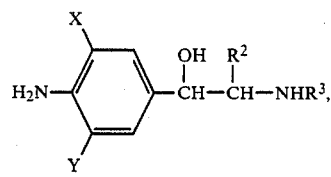

13 Claims, No Drawings

PROMOTING PRODUCTION OF USEFUL LIVESTOCK WITH SILYLATED AMINOPHENYLETHYLAMINE DERIVATIVES

This application is a continuation-in-part of application Ser. No. 709,624, filed Mar. 8, 1985, now U.S. Pat. No. 4,670,423.

The present invention relates to a method for promoting production of useful livestock, new aminophenylethylamine derivatives, and the preparation thereof.

The use of feedstuff additives to achieve higher weight gains and improved feed utilization in livestock nutrition, especially in the fattening of pigs, cattle and poultry, is already extensively practiced.

1. It has been found that the monosilylated aminophenylethylamine derivatives of the general formula (I)

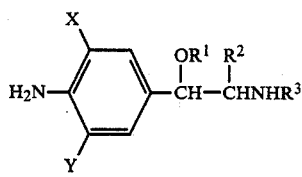
(I)

in which
X and Y are identical or different and represent hydrogen, halogen or CN,
$R^1$ represents the radical

$R^2$ represents hydrogen or methyl,
$R^3$ represents t-butyl, isopropyl, monofluoro-t-butyl or 1-cyclohexyl-ethyl, and
$R^4$, $R^5$ and $R^6$ denote a straight-chain or branched alkyl radical,
and their physiologically tolerated salts can be used in a method for promoting production of useful livestock, which is characterized in that the compounds of the formula I are administered to the useful livestock at the start of the rearing period.

The compounds of the formula (I) are in the form of diastereomers, enantiomers or in the form of their mixtures.

2. The new compounds of the general formula (I)

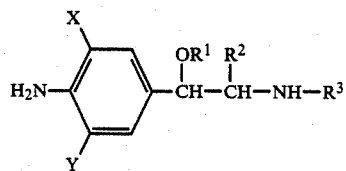
(I)

in which
X and Y are identical or different and represent hydrogen, halogen br Cn,
$R^1$ represents the radical

in which
$R^4$, $R^5$ and $R^6$ denote a straight-chain or branched alkyl radical,
$R^2$ represents hydrogen or methyl,
$R^3$ represents monofluoro-t-buyl or 1-cyclohexyl-ethyl,
and their physiologically tolerated salts, have been found.

3. The new compounds of the formula (I)

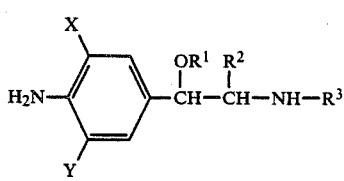
(I)

in which
X and Y are identical or different and represent hydrogen, halogen or CN,
$R^1$ represents the radical

in which
$R^4$, $R^5$, and $R^6$ denote a straight-chain or branched alkyl radical,
$R^2$ represents hydrogen or methyl,
$R^3$ represents monofluoro-t-butyl or 1-cyclohexyl-ethyl,
are obtained
(a) by reacting compounds of the formula (II)

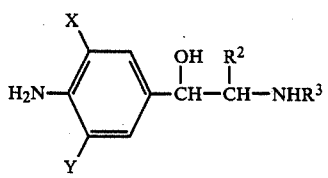
(II)

in which X, Y, $R^2$ and $R^3$ have the abovementioned meaning, with silylating agents of the formula (III)

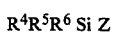
(III)

in which
Z denotes halogen, CN, $OSO_2$—$CF_3$; —O—Si—$R^4R^5R^6$ or —O—$SO_2$—O—Si—$R^4R^5R^6$, and
$R^4$, $R^5$ and $R^6$ have the abovementioned meaning, or
(b) reacting compounds of the formula (IV)

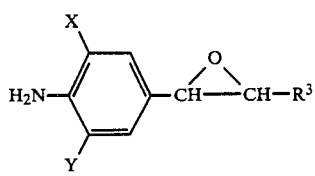

in which X, Y and $R^3$ have the abovementioned meaning, with compounds of the formula (V)

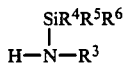

in which $R^3$, $R^4$, $R^5$ and $R^6$ have the abovementioned meaning.

4. Compounds of the formula (II)

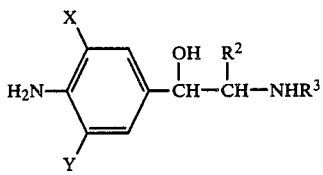

in which
X and Y, independently of one another, represent hydrogen, halogen or CN,
$R^2$ represents hydrogen or methyl, and
$R^3$ represents monofluoro-t-butyl or 1-cyclohexylethyl,
are new.

5. The compounds of the formula (II)

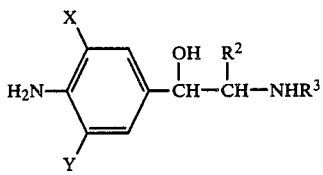

in which X, Y, $R^2$ and $R^3$ have the meaning indicated in 4. (above) are obtained by
(a) reducing compounds of the formula (VI)

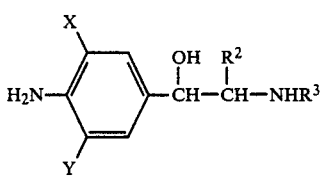

in which X, Y, $R^2$ and $R^3$ have the abovementioned meaning, catalytically or with suitable reducing agents such as, for example, sodium borohydride, sodium cyanoborohydride etc., or
(b) reacting compounds of the formula (IV)

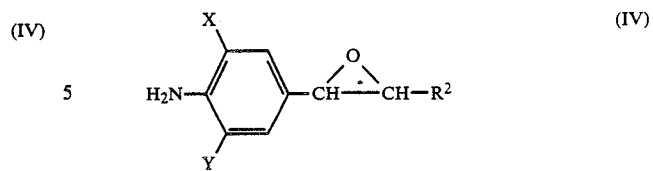

in which $R^2$ has the abovementioned meaning, with an amine of the formula (VII)

$H_2N-R^3$,  (VII)

in which $R^3$ has the abovementioned meaning, or
(c) in the case of compounds of the formula (II) in which
X, Y and $R^3$ have the abovementioned meaning, and
$R^2$ represents hydrogen,
by reacting compounds of the formula (VIII)

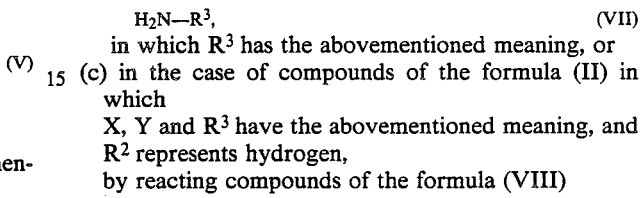

in which X and Y have the abovementioned meaning, with compounds of the formula (VII)

$H_2N-R^3$  (VII)

in which $R^3$ has the abovementioned meaning, in the presence of a reducing agent such as, for example, sodium borohydride.

6. It has been found that the compounds of the formula (II)

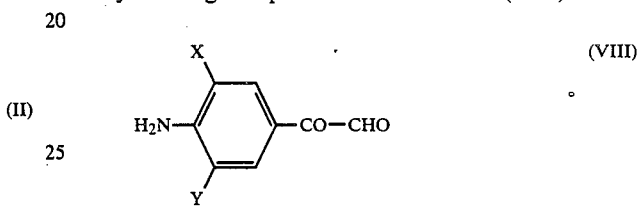

in which
X and Y, independently of one another, represent hydrogen, halogen or CN,
$R^2$ represents hydrogen or methyl, and
$R^3$ represents monofluoro-t-butyl or 1-cyclohexylethyl
and their physiologically tolerated salts have excellent production-promoting, in particular growth-promoting, action in livestock; for example they bring about an improvement in the meat/fat ratio in favor of meat.

The compounds of the formula (II) are in the form of diasteromers or of enantiomers or of mixtures thereof.

The method according to the invention according to 1. (above) exhibits excellent growth-promoting effects in useful livestock and brings about a shift in the meat/fat ratio in favor of meat.

The phenylethylamine derivatives of the general formula (I) which are preferably used in the method according to the invention are those in which
X and Y represent chlorine,
$R^2$ represents hydrogen and
$R^1$ and $R^3$ have the abovementioned meanings,
and their physiologically tolerated salts.

The phenylethylamine derivatives of the formula (I) which are particularly preferably used are those in which X and Y represent chlorine, and
$R^1$ represents $Si(CH_3)_2CH(CH_3)CH(CH_3)_2$ or $Si(CH_3)_2C(CH_3)_2CH(CH_3)_2$,
$R^2$ represents hydrogen, and
$R^3$ has the abovementioned meaning, and their physiologically tolerated salts.

Very particularly preferred compounds of the formula (I) are those in which the radical $R^3$ represents 1-cyclohexylethylamine, particular mention being made of those diastereomers in which the absolute configuration relative to C1 of the amine radical is R.

In the method according to the invention, compounds of the formula I are administered in suitable formulations to useful livestock, preferably on one occasion at the start of the rearing period. The term single administration has been chosen for this type of treatment.

Substances which improve the production of agricultural useful livestock can be administered either orally or parenterally, it being possible for the duration of administration to vary widely. As a consequence of the residue problem, administration up to immediately before slaughter of the livestock is impossible for many substances. If the substance is administered in the mixed feed, the feed to which the active compound has been added must be discontinued a defined time before slaughter and replaced by a feed containing no active compound, which frequently entails difficulties in practice. The essential advantage of a single administration is that the administration of the substance can be carried out without problems at exactly the desired time. If the duration of the effect and the residue behavior are known, with correct administration it is possible for the favorable effect of the administration of the substance to be utilized as far as possible without residues still being present in the carcase.

The following useful livestock may be mentioned as examples of livestock for which the method according to the invention can be used, for example, for promoting and accelerating growth and for improving feed conversion: warm-blooded species such as cattle, pigs and poultry, for example chickens.

The amounts of the active compounds which is administered to the livestock to achieve the desired effect can, because of the favorable properties of the active compounds, be varied widely. It is preferably about 0.001 to 50 mg/kg, in particular 0.1 to 10 mg/kg, of body weight.

The active compounds are administered to the livestock by customary methods. The mode of administration depends, in particular, on the species, the behavior and the state of health of the livestock. Thus, administration can be effected orally or parenterally.

The method is particularly suitable for parenteral administration, the active compounds being administered in the form of formulations with suitable, preferably nonaqueous, tolerated solvents or diluents.

Suitable formulating agents are preferably physiological vegetables such as, for example, sesame oil, groundnut oil or maize kernel oil. These oils, as well as other synthetic glycerides such as, for example, Miglycol ® or Myritol ®, can be thickened by suitable additives such as, for example, hardened castor oil or Al monostearate. The distribution and retention time in the animal can be varied within wide limits by such combinations.

The active compounds can be administered orally in pure form or in formulated form, that is to say mixed with non-toxic inert vehicles of any desired type.

The active compounds are, where appropriate, administered in formulated form together with pharmaceutically active compounds, mineral salts, trace elements, vitamins, proteins, fats, colorants and/or flavorings.

Oral administration is preferably effected together with the feed, the active oompounds being added to the total amount or only parts of the feed, as required.

On oral administration by customary methods, the active compounds are admixed to the feed by simply mixing, preferably in finely divided form or in formulated form mixed with edible, non-toxic vehicles, where appropriate in the form of a premix or a feed concentrate.

The feed can contain, for example, the active compounds in a concentration by weight of about 0.01 to 50° C., in particular 0.1 to 50 ppm, the optimal level of the concentration of the active compounds in the feed depends, in particular, on the amount of feed consumed by the livestock and can readily be determined by all those skilled in the art.

The nature of the feed and its composition has no relevance in this context. It is possible to use all conventional or special feed compositions which preferably contain the customary balance, which is necessary to ensure a balanced nutrition, with respect to energy and protein provision as well as the supply of vitamins and minerals. The feed can be composed of, for example, individual feedstuffs of vegetable materials, for example hay, roots, cereals and cereals by-products, and food of animal origin, for example meat, fats, milk powder, bone meal and fish products. Further individual feedstuffs are vitamins, for example vitamin A, D complex and B complex, proteins, aminoacids, for example DL-methionine, and inorganic substances, for example calcium carbonate and sodium chloride.

Mixed and compound feedstuffs are supplementary feeds. They contain the active compounds in addition to individual feedstuffs of vegetable and animal origin, such as, for example, rye flour, oorn flour, soy bean flour, mineral salts and vitamins and synthetic aminoacids. They can be prepared by the customary mixing methods.

Example for the composition of a chicken rearing feed which contains the active compound:

200 g of wheat, 340 g of corn , 361 g of coarse soy bean meal, 60 g of beef tallow, 15 g of dicalcium phosphate, 10 g of calcium carbonate;

2.5 g of active compound premix consist of, for example, 10 mg of active compound, 1 g of DL methionine and enough soy bean meal to give 2.5 g of premix.

Example for the composition of a pig rearing feed which contains an active compound:

630 g of coarse feed cereal meal (composed of 200 g of corn , 150 g of coarse barley meal, 150 g of coarse oat meal and 130 g of coarse wheat meal), 80 g of fish meal, 60 g of coarse soy bean meal, 60 g of cassava meal, 38 g of brewers' yeast, 50 g of vitamin/mineral mixture for pigs, 30 g of linseed cake meal, 30 g of corn gluten feed, 10 g of soy bean oil, 10 g of sugar cane molasses and 2 g of active compound premix (composition, for example as for chicken feed) provide, after careful mixing, 1 kg of feed.

The feed mixes indicated are designed preferably for the rearing and fattening of chickens and pigs respectively However, they can also be used, in the same or similar composition, for the rearing and fattening of other livestock.

Some of the compounds of the formula (I) are new. The new compounds of the formula (I) are summarized under 2. (above). They can be obtained by the preparation process (a) and (b) which is detailed under 3. (above).

Process (3a) can be represented by the following diagram

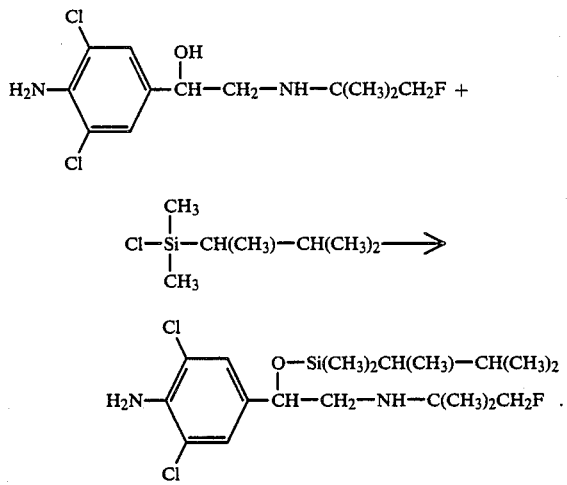

The compounds of the formula (II) are new and can be prepared by one of the processes indicated below.

The compounds of the formula (III) are known.

The reaction of the compounds of the formulae (II) and (III) is carried out by generally known processes. In general, they are used in approximately equimolar ratio. However, it may be advantageous to use the silylating agent of the formula (III) in an excess of up to 300% relative to the compound of the formula (I).

The processes can be carried out in the presence of diluents. Suitable diluents are all inert organic solvents. These particularly include aliphatic and aromatic, optionally halogenated, hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl and dibutyl ether, glycol dimethyl ether and diglycol dimethyl ether, tetrahydrofuran and dioxane, additionally ketones, such as acetone, methyl ethyl, methyl isopropyl and methyl isobutyl ketone, also esters such as methyl and ethyl acetate, furthermore nitriles, such as, for example, acetonitrile and propionnitrile, benzonitrile and glutarodinitrile, in addition amides such as, for example, dimethylformamide, dimethylacetamide and N-methylpyrrolidone, and dimethyl sulphoxide, tetramethylene sulphone and hexamethylphosphoric triamide.

The process can be carried out in the presence of catalysts. The catalysts which can preferably be used are: imidazole, triazole or diisopropylethylamine.

The reaction temperature is between about 0° C. and 130° C., preferably between about 20° C. and 60° C. The process is preferably carried out under atmospheric pressure.

Working up is carried out in the customary manner.

As already mentioned, the compounds of the formula (II) are new. Preferred compounds of the formula (II) which may be mentioned are those
in which
X and Y represent Cl,
$R^2$ represents hydrogen, and
$R^3$ represents monofluoro-t-butyl or 1-cyclohexylethyl.

Very particularly preferred compounds of the formula (I) which may be mentioned are those in which $R^3$ represents 1-cyclohexylethyl, and the absolute configuration of Cl of the amine radical is R.

The compounds of the formula (II) are prepared by one of the processes a–c generally indicated at 5. (above). The starting compounds used in them are known or can be prepared by generally known processes of chemistry.

Processes a–c are also carried out in a manner known per se.

In general, the starting compounds are used in approximately equimolar ratio. The reducing agents can be used in 1–10-fold excess.

The reaction can be carried out in the presence of the diluents mentioned for process 3a.

In general, it is carried out at temperatures from 0° to 130° C., preferably between 20 and 60° C. It is preferably carried out under atmospheric pressure.

The working up is carried out in a manner known per se.

As already mentioned, the compounds of the formula (II) can be used as production-promoters for livestock.

The following useful and ornamental livestock may be mentioned as examples of livestock in which the active compounds of the formula (II) can be used for promoting, in particular promoting production, and accelerating growth and for improving feed conversion:

Warm-blooded species such as cattle, pigs, horses, sheep, goats, cats, dogs, rabbits, and fur-bearing livestock, for example mink and chinchilla, poultry, for example chickens, geese, ducks, turkeys, pigeons, parrots and canaries, and cold-blooded species such as fish, for example carp, and reptiles, for example snakes.

The amounts of the active compounds which is administered to the livestock to achieve the desired effect can, because of the favorable properties of the active compounds, be varied widely. It is preferably about 0.01 to 50, in particular 0.1 to 10, mg/kg of body weight per day. The duration of administration can be from a few hours or days up to several years. The appropriate amount of the active compound and the appropriate duration of administration depend, in particular, on the species, the age, the sex, the state of health and the manner of housing and feeding of the livestock and can readily be determined by all those skilled in the art.

The active compounds of the formula (II) are administered to the live-stock by customary methods. The mode of administration depends, in particular, on the species, the behavior and the state of health of the livestock. Thus, the administration can be carried out orally or parenterally, once or several times a day, at regular or irregular intervals.

The active compounds according to the invention are particularly suitable for parenteral administration, being converted with suitable, preferably non-aqueous, tolerated solvents or diluents into a formulation which can be administered.

Suitable formulating agents are preferably physiological vegetables, such as, for example, sesame oil, groundnut oil or corn kernel oil. These oils, as well as other synthetic triglycerides, such as, for example, Miglycol ® or Myritol ®, can be thickened by suitable additives, for example hardened castor oil or Al monostearate. It is possible by such combinations to vary within wide limits the viscosity and thus the depot effect.

Furthermore, implants of silicone or high molecular weight polyglycols or other physiologically tolerated polymers are possible.

For reasons of expediency, oral administration is frequently to be preferred, in particular in the rhythm of intake of food and/or drink by the livestock.

The active compounds can be administered as a pure substance mixture or in formulated form, that is to say mixed with non-toxic inert vehicles of any desired nature, for example with vehicles and in formulations as are customary for nutritive compositions.

The active compounds are administered, where appropriate in formulated form, together with pharmaceutically active compounds, mineral salts, trace elements, vitamins, proteins, fats, colorants and/or flavorings, in a suitable form.

Oral administration is preferably effected together with the feed and/or drinking water, the active compounds being added, as required, to the total amount or only parts of the feed and/or the drinking water.

On oral administration by customary methods, the active compounds are added to the feed and/or drinking water by simply mixing as a pure substance mixture, preferably in finely divided form or in formulated form mixed with edible, non-toxic vehicles, where appropriate in the form a premix or of a feed concentrate.

The feed and/or drinking water can contain, for example, the active compounds in a concentration by weight of about 0.01 to 50, in particular 0.1 to 10, ppm. The optimal level of the concentration of the active compounds in the feed and/or drinking water depends, in particular, on the amount of feed and/or drinking water consumed by the livestock, and can readily be determined by all those skilled in the art.

On parenteral administration, the optimal dose depends, in particular, on the frequency of administration, the species and the age and weight of the livestock.

The nature of the feed and its composition has no relevance in this context. It is possible to use all conventional or special feed compositions which preferably contain the customary balance, which is necessary for a balanced nutrition, of energy providers and builders, including vitamins and minerals. The feed can be composed of, for example, vegetable materials, for example hay, roots, cereals and cereals by-products, animal materials, for example meat, fats, bonemeal and fish products, vitamins, for example vitamin A, D complex and B complex, proteins, amino acids, for example DL-methionine, and inorganic substances, for example calcium carbonate and sodium chloride.

Feed concentrates contain the active compounds in addition to edible substances, for example rye flour, corn flour, soy bean flour or calcium carbonate, where appropriate with other nutrients and builders, and proteins, mineral salts and vitamins. They can be prepared by the customary mixing methods.

Preferably in premixes and feed concentrates, the active compounds can optionally also be protected from air light, and/or moisture by agents suitable for covering their surfaces, for example with non-toxic waxes or gelatin.

EXAMPLE 1A

Effect of a single administration on the body weight gain of rats

For the trial, female Wistar rats which were housed in Makrolon cages (3 animals per cage) were used. After a 3-day adaptation period, the 21-day experiment was started. Both the effect of a single oral administration and the effect of a single subcutaneous administration on the body weight gain of the rats was investigated. 12 animals were used for each treatment. The active compounds were dissolved in placebo A 1040 (86% polyethylene glycol, 10% glycerol, 4% water) and administered either by gavage (5 mg of active compound in 1.0 ml of placebo) or subcutaneously (5 mg of active compound in 0.2 ml of placebo).

Active compound I=N-[2-(4-amino-3,5-dichlorophenyl)-2-hydroxy-ethyl]-N-t-butylamine Active compound II=N-[2-(4-amino-3,5-dichlorophenyl)-2-(1,2-dimethylpropyl-dimethylsilyloxy)-ethyl]-N-t-butylamine The results of the trial are compiled in Table 1.

TABLE 1

| Treatment | Weight increase in female Wistar rats after single dose (5 mg/animal) | | | |
|---|---|---|---|---|
| | Day 0–Day 9 g | | Day 0–Day 21 g | |
| Control (oral administration) | 15.0 | (100) | 31.1 | (100 |
| 5 mg compound I (comparison) administered orally | 21.3 | (142) | 38.7 | (124) |
| 5 mg compound II administered orally | 26.7 | (178) | 44.3 | (142) |
| Control administered subcutaneously | 14.0 | (100) | 29.7 | (100) |
| 5 mg compound I (comparison) administered subcutaneously | 22.8 | (163) | 39.5 | (132) |
| 5 mg compound II administered subcutaneously | 26.7 | (190) | 48.4 | (163) |

EXAMPLE 1B

Rat-Feeding Trial

Female laboratory rats weighing 90–110 g of the type SPF Wistar (bred by Hagemann) are fed ad lib with standard rat feed to which the desired amount of active compound is added. Each section of the trial is carried out with feed from the same batch so that differences in the composition of the feed cannot impair the comparability of the results.

The rats receive water ad lib.

12 rats form each trial group and thy are fed with feed to which the desired amount of active compound is added. A control group receives feed containing no active compound. The mean body weight and the variation in the body weights of the rats is the same in each trial group, so that comparability of the trial groups with one another is ensured.

The weight gain and feed consumption during the 13-day trial are determined.

The results which are shown in the following table are obtained.

TABLE 2

| | Rat feeding trial | | |
|---|---|---|---|
| Active compound | Dose ppm | Number of animals | Gain (relative to control) |
| Control | — | 48 | 100 |
| Example 1 | 25 | 12 | 133 |
| Example 7 | 25 | 24 | 132 |
| Example 8 | 25 | 24 | 128 |

Peparation examples

EXAMPLE 1C 1-(4-Amino-3,5-dichloro-phenyl)-2-(1-cyclohexyl-ethylamino)-ethanol

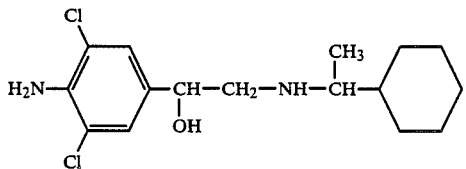

21 g of 4-amino-3,5-dichloro-ω-(1-cyclohexylethylamino)acetophenone are dissolved in 180 ml of methanol and 36 ml of water, and a solution of 5.8 g of sodium borohydride in 18 ml of water is added dropwise, the pH being maintained between 3 and 7 by addition of approximately 10% strength hydrochloric acid. After the reaction is complete, the mixture is made strongly acid and is evaporated. The residue is made basic with ammonia, and the mixture is extracted with ethyl acetate, the ethyl acetate phase is washed twice with water, dried and evaporated. The resulting crystals are stirred with heptane and filtered off with suction. 13.3 g of colorless crystals of melting point: 106°–108° C. are obtained.

The following was prepared in analogy to Example 1:

EXAMPLE 2

1-(4-Amino-3,5-dichlorophenyl)-2-(1-cyclohexyle-thylamino)propanol, isolated as hydrochloride of melting point: 265° C.

EXAMPLE 3

1-(4-Amino-3,5-dichlorophenyl)-2-[(R)-1-cyclohexyl-ethylamino]-ethanol 10.9 g (29.8 mmol) of 4-amino-3,5-dichloro-ω-((R)-1-cyclohexyl-ethylamino)-acetophenone hydrochloride (obtained from 4-amino-3,5-dichloro-ω-bromo-acetophenone by reaction with (R)-1-cyclohexyl-ethylamine are dissolved in 75 ml of methanol and 18 ml of water and, at a pH between 2 and 7, a solution of 2.5 g of sodium borohydride in 8 ml of water is added dropwise. The pH is adjusted to 9, and concentration and extraction with ethyl acetate are carried out. The ethyl acetate phase is washed with water, dried and concentrated. The crystalline product is stirred with heptane, filtered off with suction and washed with heptane. 6.5 g of a colorless substance of melting point 110° to 116° C. are obtained.

The two diastereomers are separated by fractional recrystallization from acetonitrile:

Physical data:

| Diastereomer A: | Melting point: 142° C. |
|---|---|
| $[\alpha]^{20}_{589} = 50.65$ | (c = 0.69, methanol) |
| Diastereomer B: | Melting point: 108–111° C. |
| $[\alpha]^{20}_{589} = 27.26$ | (c = 0.8576, methanol) |

The absolute configurations on the ethanol C atom 1 of the two diastereomers A and B are as yet indefinite.

EXAMPLE 4

1-(4-Amino-3,5-dichlorophenyl)-0-(1,2-dimethylpropyl-dimethylsilyl)-2-(1-cyclohexylethylamino)-ethanol

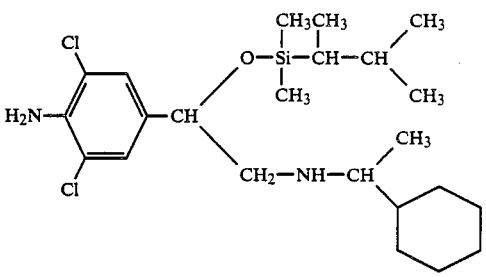

2.36 g (7.15 mmol) of the compound from Example 1 are added to 937 mg (14.3 mmol) of imidazole in 15 ml of absolute DMF. Now, at 0°–5° C., 1.52 g of dimethyl-1,2-dimethyl-propylsilyl chloride are added. The mixture is stirred while cooling in ice for 2 hours, then evaporated, and the residue is taken up in toluene/water, the phases are separated, the toluene phase is washed 4 x with water, dried, evaporated, and residues of solvent are removed at the oil pump. 3.2 g of an almost colorless oil are obtained.

Rf: 0.62.

Rf: substance Example 1: 0.24.

TLC Merck aluminum roll, silica gel 60, F 254, layer thickness 0.2 mm.

Mobile phase: toluene/ethanol in the ratio by volume 6:1.

EXAMPLE 5

In analogy to the procedure in Example 4, 2.36 g of diastereomer A (obtained as in Example 3) are reacted with 1.52 g of dimethyl-1,2-dimethylpropylsilyl chloride. The silyl derivative corresponding to diastereomer A is obtained. It has a Rf value: 0.49 (TLC Merck aluminum roll, silica gel 60 F 254, layer thickness 0.2 mm). Mobile phase toluene/ethanol in the ratio by volume 10:1.

EXAMPLE 6

The dimethyl-1,2-dimethyl-propyl-silyl derivative corresponding to diastereomer B is obtained with diastereomer B (obtained as in Example 3) in analogy to the procedure in Example 5. Rf value 0.49 (GLC Merck aluminum roll, silica gel 60 F 254, layer thickness 0.2 mm). Mobile phase toluene/ethanol in the ratio by volume 10:1.

EXAMPLE 7

1-(4-Amino-3,5-dichloro-phenyl)-2-(2-fluoro-1,1-dimethylethyl-amino)-ethanol

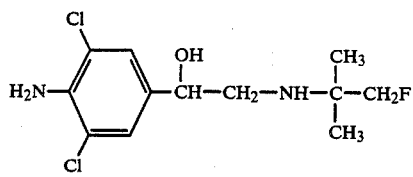

8.5 g of 4-amino-3,5-dichloro- -(2-fluoro-1,1-dimethyl-ethylamino)-acetophenone hydrochloride are dissolved in 60 ml of methanol and 15 ml of water, and a solution of 2.9 g of sodium borohydride in 10 ml of water is added dropwise, the pH being maintained between 3 and 7 by addition of 2 N hydrochloric acid. After the reaction is complete, the mixture is made strongly acid and is concentrated. The residue is made basic with ammonia, extracted with ethyl acetate, and the ethyl acetate phase is washed twice with water, dried and concentrated. The resulting crystals are recrystallized from a little acetonitrile. 5.4 g of colorless crystals of melting point 110° C. are obtained.

EXAMPLE 8

1-(4-Amino-3,5-dichlorophenyl)-0-(1,2-dimethylpropyl-dimethylsilyl)-2-(2-fluoro-1,1-dimethyl-ethylamino)ethanol

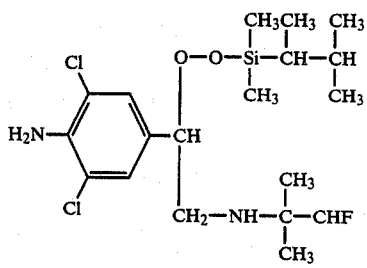

5.9 g of 1-(4-amino-3,5-dichlorophenyl)-2-(2-fluoro-1,1-dimethyl-ethyl-amino)-ethanol and 4 g of imidazole are dissolved in 60 ml of dry dimethylformamide and, at 0° C., 7.26 g of pentyl-dimethylchlorosilane are added dropwise. The mixture is then left to stir at room temperature for 2 hours and is then evaporated in a rotary evaporator. 100 ml of toluene are added to the residue from evaporation, and the solution is washed three times with water, dried, concentrated and dried at 80° C. under high vacuum. 7.2 g of pale yellow oil with an Rf value of 0.63 (toluene/ethanol=10/1) are obtained.

EXAMPLE 9

1-(4-Amino-3-cyano-phenyl)-0-(1,2-dimethylpropyl-dimethylsilyl)-2-isopropylamino-ethanol of Rf value: 0.46.

TLC Merck aluminum roll, silica gel 60, F 254, layer thickness 0.2 mm.

Mobile phase: toluene/ethanol in the ratio by volume 3:1.

EXAMPLE 10

1-(4-Amino-3,5-dichlorophenyl)-0-(1,2-dimethylpropyl-dimethylsilyl)-2-[(R)-1-cyclohexyl-ethylamino]-ethanol, prepared from Example 3 with dimethyl-1,2-dimethylpropylsilyl chloride.

RF value: 0.49 (mobile phase: toluene/ethanol 10:1).

(EXAMPLE 11

1-(4-Amino-3,5-dichlorophenyl)-0-(dimethyl-hexyl-silyl)-2-(1-cyclohexyl-ethylamino)-ethanol

EXAMPLE 12

1-(4-Amino-3,5-dichlorophenyl)-0-(dimethyl-hexyl-silyl)-2-[(R)-1-cyclohexyl-ethylamino)-ethanol

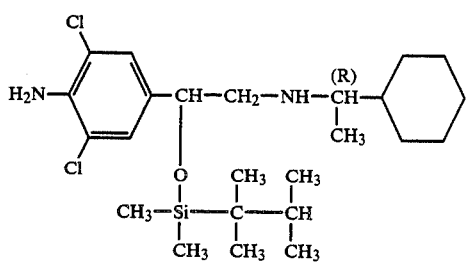

Preparation in analogy to Example 4 by reaction of Example 3 with dimethyl-hexylsilyl chloride in DMF in the presence of imidazole at 60° C. for 24 hours.

Rf value: 0.57; mobile phase: toluene/ethanol in the ratio by volume 10:1.

It is understood that the specification and examples are illustrative but not limitative of the present invention and that other embodiments within the spirit and scope of the invention will suggest themselves to those skilled in the art.

We claim:

1. A method for modifying the growth of useful livestock comprising administering to such livestock an amount effective therefor of a monosilylated aminophenylethylamine derivative of the formula

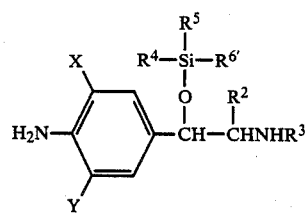

in which

X and Y are identical or different and represent hydrogen or CN, $R^2$ represents hydrogen or methyl, $R^3$ represents t-butyl, isopropyl, monofluoro-t-butyl or 1-cyclohexyl-ethyl, and $R^4$, $R^5$ and $R^6$ denote a straight-chain or branched alkyl radical, or a physiologically tolerated salt thereof.

2. The method according to claim 1, in which $R^3$ represents monofluoro-t-butyl or 1-cyclohexyl-ethyl.

3. The method according to claim 1, wherein such compound is 1-(4-amino-3,5-dichlorophenyl)-0-(1,2-dimethylpropyl-di-methylsilyl)-2-(2-fluoro-1,1-dimethyl-ethylamino) ethanol of the formula

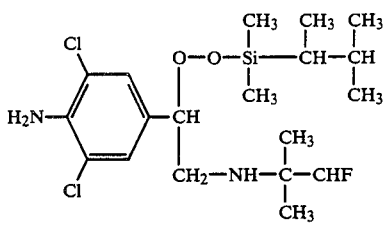

or a physiologically tolerated salt thereof.

4. The method according to claim 1, wherein such compound is 1-(4-amino-3,5-dichlorophenyl)-0-(dimethylhexylsilyl)-2-[R]-1-cyclohexyl-ethylamino)-ethanol of the formula

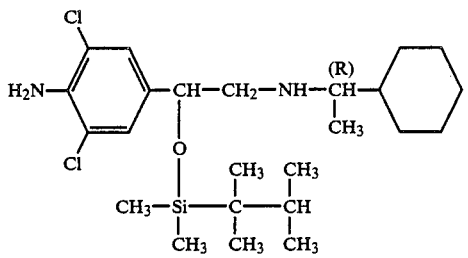

or a physiologically tolerated salt thereof.

5. A growth-modifying composition comprising an edible food base and a livestock-promoting effective amount of a monsilylated aminophenylethylamine derivative of the formula

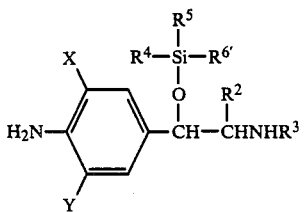

in which
X and Y are identical or different and represent hydrogen or CN,
$R^2$ represents hydrogen or methyl,
$R^3$ represents t-butyl, isopropyl, monofluoro-t-butyl or 1-cyclohexyl-ethyl, and
$R^4$, $R^5$ and $R^6$ denote a straight-chain or branched alkyl radical,
or a physiologically tolerated salt thereof.

6. A compound of the formula

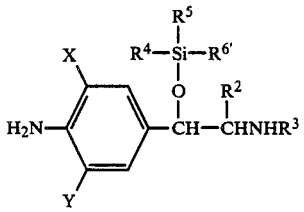

in which
X and Y are identical or different and represent hydrogen, halogen or CN,
$R^4$, $R^5$ and $R^6$ denote a straight-chain or branched alkyl radical,
$R^2$ represents hydrogen or methyl, $R^3$ represents monofluoro-t-butyl or 1-cyclohexyl-ethyl,
or a physiologically tolerated salt thereof.

7. A compound according to claim 6, wherein such compound is 1-(4-amino-3,5-dichlorophenyl)-0-(1,2-dimethylpropyl-di-methylsilyl)-2-(2-fluoro-1,1-dimethyl-ethyalmino) ethanol of the formula

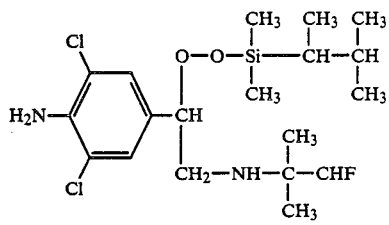

or a physiologically tolerated salt thereof.

8. A compound according to claim 6, wherein such compound is i-(4-amino-3,5-dichlorophenyl)-0-(dimethylhexylsilyl)-2-1-cyclohexyl-ethylamino)-ethanol of the formula

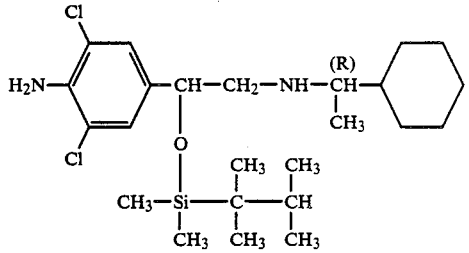

or a physiologically tolerated salt thereof.

9. A livestock-growth-modifying composition comprising an amount effective therefor of a compound or salt according to claim 6.

10. A compound of the formula

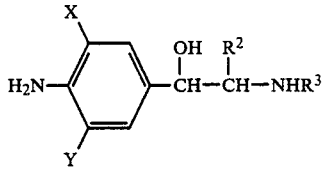

in which
X and Y, independently of one another, represent hydrogen, halogen or CN,
$R^2$ represents hydrogen or methyl,
$R^3$ represents 1-cyclohexyl-ethyl.

11. 1-(4-Amino-3,5-dichloro-phenyl)-2-(1-cyclohexyl-ethyl-amino)-ethanol of the formula

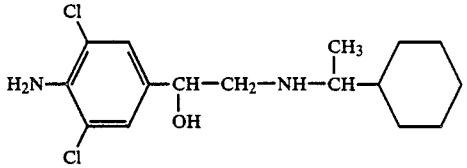

or a physiologically tolerated salt thereof.

12. A growth-modifying composition comprising an edible food base and a growth-modifying effective amount of a compound or salt according to claim 11.

13. A method for modifying the growth of useful livestock comprising administering to such livestock an amount effective therefor of a compound or salt according to claim 11.

* * * * *

UNITED STATES PATENT AND TRADEMARK OFFICE
CERTIFICATE OF CORRECTION

PATENT NO. : 4,806,667

DATED : February 21, 1989

Page 1 of 2

INVENTOR(S) : Horst Böshagen, et al

It is certified that error appears in the above-identified patent and that said Letters Patent is hereby corrected as shown below:

Title Page, under "U.S. Patent Documents", line 1 — Delete "Kock" and substitute --Keck--

Title Page, Abstract, line 3 — Correct spelling of --aminophenylethylamine--

Title Page, Abstract, line 13 — Correct spelling of --radical--

Col. 1, line 67 — Delete "Cn" and substitute --CN--

Col. 2, line 12 — After "monofluoro-t-" correct spelling of --butyl--

Col. 6, line 12 — Delete "oompounds" and substitute --compounds--

Col. 6, line 45 — Delete "oorn" and substitute --corn--

Col. 10, line 12 — After "cover" insert -- - --

Col. 10, Table 1, line 1 of last column — Delete "(100" and substitute --(100)--

Col. 10, line 62 — Delete "thy" and substitute --they--

Col. 11, line 15 — Correct spelling of --Preparation--

Col. 15, line 30 — Delete "livestock-promoting" and substitute --growth-modifying--

UNITED STATES PATENT AND TRADEMARK OFFICE
CERTIFICATE OF CORRECTION

PATENT NO. : 4,806,667                Page 2 of 2

DATED : February 21, 1989

INVENTOR(S) : Horst Böshagen, et al

It is certified that error appears in the above-identified patent and that said Letters Patent is hereby corrected as shown below:

Col. 16, line 19        Delete "i" and substitute --1--
Col. 16, line 20        After "2-" insert --[R]--

Signed and Sealed this

Third Day of April, 1990

Attest:

HARRY F. MANBECK, JR.

*Attesting Officer*        *Commissioner of Patents and Trademarks*